United States Patent [19]
Kula et al.

[11] Patent Number: 5,134,073
[45] Date of Patent: Jul. 28, 1992

[54] MICROBIOLOGICALLY PRODUCED N-ACETYL-2,3-DIDEHYDROLEUCINE ACYLASE

[75] Inventors: Maria-Regina Kula, Niederzier/Hambach; Matthias Kittelmann, Freiburg, both of Fed. Rep. of Germany

[73] Assignee: Degussa Aktiengesellschaft, Fed. Rep. of Germany

[21] Appl. No.: 472,388

[22] Filed: Feb. 1, 1990

[30] Foreign Application Priority Data

Feb. 4, 1989 [DE] Fed. Rep. of Germany ....... 3903324

[51] Int. Cl.$^5$ .................... C12N 9/80; C12N 1/00; C12N 1/12; C12P 13/06
[52] U.S. Cl. .................. 435/228; 435/822; 435/252.1; 435/116
[58] Field of Search ............... 435/228, 252.1, 116, 435/822

[56] References Cited
PUBLICATIONS

Nishida et al., Enzyme Microb. Technol., vol. 9, pp. 479–483, 1987.
Hummel et al., Appl. Microbiol. Biotechnol., vol. 27, pp. 283–291, 1987.

*Primary Examiner*—Douglas W. Robinson
*Assistant Examiner*—Mike Meller
*Attorney, Agent, or Firm*—Cushman, Darby & Cushman

[57] ABSTRACT

A novel N-Acetyl-2,3-didehydroaminoacid-acylase is obtained by cultivating Zoogloea ramigera DSM 4306. The new enzyme can be used in a coupled enzyme system with an L-Leucinedehydrogenase for the enzymatic conversion of N-Acetyl-2,3-didehydroleucine to L-Leucine, D- or L-tryptophylglycine to D- or L- tryptophaneamide and glycine, as well as other tryptophanedipeptides to tryptophaneamides and free amino acids.

3 Claims, No Drawings

MICROBIOLOGICALLY PRODUCED N-ACETYL-2,3-DIDEHYDROLEUCINE ACYLASE

The present invention relates to an enzyme which has not been previously described and which catalyzes reactions of the following type:

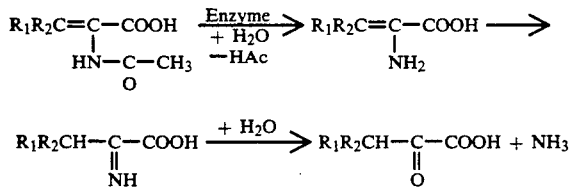

Particularly good conversions are obtained with $R_1=(CH_3)_2CH-$ and $R_2=H-$, as well as with $R_1=CH_3-$ and $R_2=H-$ ($=$2-acetylamino acrylic acid).

Nakamichi et al. (Appl. Microbiol. Biotechnol. 19, pp. 100–105, 1984, and Appl. Biochem. Biotechnol. 11, pp. 367–376, 1985) as well as Nishida at al. (Enzyme Microb. Technol. 9, pp. 479–483, 1987) describe the occurrence of acylases which hydrolyze 2-acetylamino cinnamic acid (=N-acetyl-2,3-didehydrophenylalanine) to phenyl pyruvate and acetic acid in bacterial cells of the species Bacillus sphaericus and Alcalignes faecalis. Nothing was published about the substrate specificity of these enzymes. Hummel et al. (Appl. Microbiol. Biotechnol. 25, pp. 175–185, 1987) isolated a 2-acetylamino cinnamic acid acylase from a strain of the genus Brevibacterium. However, this enzyme is not capable of splitting other N-acetyl-2,3-didehydroamino acids.

The N-acetyl-2,3-didehydroleucine acylase of the invention is characterized by the following qualities:

1) Reactivity:
It splits off the acetyl group from N-acetyl-2,3-didehydroleucine, at which time acetic acid and, after consecutive chemical reactions, 12-keto-4-methyl valeric acid and ammonia arise as end products;

2) Substrate specificity:
It hydrolyzes both various N-acetyl-2,3-didehydroamino acids such as N-acetyl-2,3-didehydrovaline, N-acetyl-2,3-didehydroisoleucine, 2-acetylamino cinnamic acid and 2-acetylamino acrylic acid as well as amino acid amides such as D- and L-tryptophane amide, D- and L-leucine amide and L-methionine amide but not 2,3-saturated N-acetylamino carboxylic acids such as N-acetyl leucine or N-acetyl valine;

3) Optimum pH:
The optimum pH is $9.3\pm1$;

4) pH stability:
It exhibits good stability in a pH range between 9 and 10;

5) Optimum temperature:
The optimum temperature is 55° C. at a pH of 9;

6) Temperature resistance:
At 50° C., 90% residual activity can still be demonstrated after 30 minutes incubation;

7) Influences of inhibitors and activators:
Inhibitors of serine proteases, especially phenylmethane sulfonylfluoride (0.001 mM), exert an inhibitory action, glycine accelerates the substrate splitting as a function of the concentration;

8) Molecular weight:
The molecular weight is approximately 60,000;

9) Subunits:
The molecule consists of only one unit;

10) $K_M$-value:
The $K_M$-value for the substrate N-acetyl-2,3-didehydroleucine is 4.5 mM (30° C., 0.1 M glycine buffer, pH 9).

The N-acetyl-2,3-didehydroleucine acylase of the invention can be recovered by means of a zoogloea strain which was deposited on Dec. 1, 1987 in the German Collection of Microorganisms in Gottingen under number DSM 4306.

The following qualities show that the microorganism belongs to the species Zoogloea ramigera:

It grows in slightly curved, Gram-negative rods. The cells can be moved by a polar flagellum and do not form spores. Growth occurs without nitrate strictly aerobically. No acid is formed from glucose. Catalase and oxidase reaction as well as nitrate reduction are positive, urea splitting positive, gelatin and casein decomposition positive, starch breakdown negative, denitrification negative (unusual for the genus Zoogloea). The strain contains the ubiquinone Q 9. The microorganism can be preserved as lyophilized culture. Working cultures are maintained on oblique agar tubes (N-acetyl-2,3-didehydroleucine medium).

In order to recover the N-acetyl-2,3-didehydroleucine acylase of the invention, Zoogloea ramigera DSM 4306 is cultivated in an aqueous nutrient medium containing a source for carbon and nitrogen and mineral salts at an initial pH between 7.5 and 9 aerobically at 25° to 38° C., then N-acetyl-2,3-didehydroleucine is added to the nutrient solution as inductor and the mixture is cultivated further aerobically at pH 6.5 and at 28° to 38° C., the cell mass separated and the enzyme isolated from the cells.

The enzyme can be recovered in larger amounts e.g. by cultivating Zoogloea ramigera in a known manner in a bioreactor of the desired size, e.g. with a working volume of 5 liters. The following is important for a successful culture:

A good aerating (obligatorily aerobic organism);
The presence of nutrients, e.g. in complex form as yeast extract;
A gradual subsequent introduction of the nutrients;
For growth, a pH between 7.5 and 9;
For the enzyme production, a pH of 6.5;
For the enzyme production, the presence of N-acetyl-2,3-didehydroleucine (5 to 9 g/l).

The enzyme can be recovered after digestion of the cells by a combination of known methods of enzyme purification. The enzyme can be used as a component of a coupled enzyme system with an L-leucine dehydrogenase for the enzymatic conversion of N-acetyl-2,3-didehydroleucine via the intermediary stage 2-imino-4-methyl-valeric acid or the corresponding keto acid to L-leucine. In addition, the enzyme can be used for the preparation of D- or L-tryptophyl glycine from D- or L-tryptophane amide and glycine, of D- or L-tryptophyl-D-methionine from D- or L-tryptophane amide and D-methionine as well as of L-tryptophyl-D-cysteine from L-tryptophane amide and D-cysteine.

DETAILED DESCRIPTION OF PREFERRED EMBODIMENTS

The invention is explained in more detail in the following examples. The following abbreviated formulas are used: N-acetyldehydro- for N-acetyl-2,3-didehydro- , ADL for N-acetyl-2,3-didehydroleucine, ADI for N-acetyl-2,3-didehydroisoleucine and ADV for N-acetyl-2,3-didehydrovaline.

EXAMPLE 1

Search for N-acetyldehydroleucine acylase producers 63 soil, water and sewage plant specimens were suspended and diluted with a mineral salt solution and 20 ml liquid medium (enrichment medium) were inoculated with 0.02-0.2 ml of these batches. The mineral salt solution exhibited the following composition:

| | |
|---|---|
| $K_2HPO_4$ | 3.7 g |
| $KH_2PO_4$ | 1.5 g |
| $MgSO_4.7\ H_2O$ | 0.2 g |
| $CaCl_2.2\ H_2O$ | 2.0 mg |
| $ZnSO_4.7\ H_2O$ | 0.4 mg |
| $FeCl_3.6\ H_2O$ | 0.2 mg |
| Deionized water | 1.0 l |
| pH | 7.2 |
| The enrichment medium contained: | |
| N-acetyldehydroamino acid | 3.0 g |
| Trace-element solution | 3.0 ml |
| Yeast extract | 0.2 g |
| Mineral salt solution (see above) | 1.0 l |
| pH | 7.2 |

The leucine, isoleucine and valine derivatives were used as N-acetyldehydroamino acids. Prior to the inoculation, the medium was introduced into 100 ml Erlenmeyer flasks and sterilized by autoclaving. After cooling, 0.02 ml vitamin solution, sterilized by filtration, was added to each flask (composition of the vitamin solution according to H. G. Schlegel, "Allgemeine Mikrobiologie", Thieme Verlag, 1981, p. 169).

The cultures were incubated aerobically at 28° C. in a rotary agitator at 110 rpms for 6-10 days. Densely over grown batches with an optical density at 660 nm of at least 0.7 were diluted in sterile phosphate buffer (20 mM, pH 7) in a conventional manner and plated out onto selective nutrient media with the following composition:

| | |
|---|---|
| Agar | 2.0 g |
| Yeast extract | 0.1 g |
| Enrichment medium (see above) of the particular culture | 1.0 l |
| pH | 7.2 |

The medium was autoclaved without vitamin solution and the latter not added until after the cooling of the agar before pouring out into sterile Petri dishes in the amount indicated above. Reference plates of each enrichment culture were also inoculated in parallel as described, which plates exhibited the same composition as the selective nutrient media but contained no N-acetyldehydroamino acids. The inoculated plates were incubated 3 to 10 days at 28° C. A colony was removed from each of the colony types which could be found only on the selective nutrient media but not on the reference plates and was placed in a conventional manner on the selective agar in pure culture (dilution smears, microscopy).

Strains which appeared homogeneous were then multiplied in 100 ml liquid medium (500 ml Erlenmeyer flask) at 27° C. on a rotary agitator machine at 110 rpms. The culture medium had the following composition:

| | |
|---|---|
| Yeast extract | 0.5 g |
| Peptone | 0.5 g |
| Enrichment medium (see above) of the organism to be tested | 1.0 l |
| pH | 7.2 |

After 48-60 hours, the contents of the agitator flask were centrifuged (20 min., 8,000 g in a refrigerated centrifuge) and the sedimented cells were suspended in 0.05 M potassium phosphate buffer, pH 7 (4 ml buffer per 1 g moist bacterial mass).

The microorganisms in this suspension must be digested in a customary manner (e.g. agitation with fine glass beads, ultrasound treatment, French press). For this purpose, the suspensions were compounded with glass beads (0.1 to 0.2 mm diameter) using 2 g glass beads per 1 ml cellular suspension and then mixing the mixture in a test tube for 10 minutes with a laboratory agitator (type Reax 2000, Heidolph company). Most of the organisms were able to be well digested with this method. Indissoluble cellular components and the glass beads were centrifuged off (13,000 rpms, Biofuge A, Heraeus company) and the supernatant used as enzyme source (raw extract).

The batches for the activity test contained:

| | |
|---|---|
| 0.2 M N-acetyldehydroamino acid | 0.05 ml |
| raw extract | 0.075 ml |
| 0.05M tris/HCl buffer, pH 7.2 | 0.375 ml. |

All raw extracts were tested at least with N-acetyldehydroleucine and N-acetyldehydroisoleucine but, in most cases, also with N-acetyldehydrovaline. Incubation time and raw-extract dilution were measured in such a manner that the linearity range of the following color test for the demonstration of the reaction product (0.26 mM keto acid) was not exceeded. The enzymatic reaction was stopped in the batches incubated at 30° C. by adding 0.25 ml color reagent (1 g/l 2,4-dinitrophenyl hydrazine in 2 N HCl). After further incubation at 30° C. for 10 minutes with N-acetyldehydroleucine as substrate or 25 minutes with the isoleucine or valine derivative, 1.5 ml 2,5 N NaOH was added.

The keto acid released by the enzymatic hydrolysis forms, together with the 2,4-dinitrophenyl hydrazine, a Schiff's base colored red in the alkaline whose absorption was measured in a spectral photometer at 442 nm against a batch without N-acetyldehydroamino acid (=enzyme blank). A blank reading was deducted from these extinction values which blank reading is obtained if the extinction value of a batch only with buffer (=buffer blank) is deducted from that of a batch with buffer and N-acetyldehydroamino acid but without raw extract (=substrate blank). The concentration of the product produced was determined with a calibrated reference for the corresponding keto acid. The enzyme activity is indicated in international units. One unit (U) corresponds to an amount of 1 μmole released keto acid per minute.

As table 1 shows, the strain Zoogloea ramigera ABI 1 (DSM 4306) exhibits the highest activity in the above-described test procedure and was therefore used for the production of the enzyme.

TABLE 1

Production of N-acetyldehydroamino acid acylase by means of the 7 most active microorganisms in the screening

| | Substrate: | | | | | |
|---|---|---|---|---|---|---|
| | ADL | | ADI | | ADV | |
| Strain | Specific Activity (mU/mg) | Vol. Yield (U/l) | Specific Activity (mU/mg) | Vol. Yield (U/l) | Specific Activity (mU/mg) | Vol. Yield (U/l) |
| ABI 1 | 147 | 11.5 | 19 | 1.41 | 48 | 3.72 |
| ABI 3 | 103 | 11.0 | 15 | 1.62 | 28 | 2.98 |
| ABI 5 | 100 | 9.1 | 8 | 1.21 | 29 | 2.64 |
| SZI 2 | 77 | 4.1 | 13 | 0.70 | 27 | 1.47 |
| SZI 4 | 109 | 7.1 | 12 | 0.81 | 33 | 2.14 |
| SZI 5 | 69 | 4.2 | 15 | 0.90 | 35 | 2.12 |
| SZI 7 | 129 | 10.9 | 15 | 1.49 | 30 | 2.94 |

EXAMPLE 2

Production of N-acetyldehydroleucine acylase a) Acylase fermentation with strain ABI 1 on a 5 l scale A bioreactor with 5 liter working volume was used which was equipped with a device for the automatic regulation of the pH and foam inhibition. The medium contained:

| Yeast extract | 35.0 g |
|---|---|
| Mineral salt solution (cf. example 1) | 5.0 l |
| pH | 8.3 |

After sterilization, the medium was inoculated with 500 ml of a preculture which had been cultivated for 60 hours in portions of 150 ml of the same medium in 500 ml Erlenmeyer flasks. The incubation took place at 30° C. and 100 rpms on a rotary agitator. The conditions during the growth phase of the fermentation were:

| pH | 8.3 |
|---|---|
| Temperature: | 35.0° C. |
| Concentration of dissolved oxygen (% saturation) | 80% |
| Maximum agitator speed | 300 rpms |

Specimens were taken at different times and the cell growth followed by means of turbidimetric measurement (measurement of the optical density) at 660 nm.

300 ml of a concentrated yeast extract solution sterilized by autoclaving (100 g/l in mineral salt solution as described in Example 1) were added after 10, 21 and after 24 hours each to the fermenter contents under aseptic conditions.

After approximately 25 to 30 hours incubation, when no further increase of the bacterial mass could be detected, 3.5 liters of the medium were filtered off by means of a sterilely coupled cross-current microfiltration system (type Sartocon II, 0.6 m² polyolefin membrane, pore diameter 0.2 µm, company Sartorius). The fermenter contents were passed through the filtration module by means of a hose pump at 185 liters per hour so that a pressure difference of 0.8–0.9 bar was produced between the module inlet and the module outlet. The bacterial cells and the non-separated liquid medium were returned into the fermenter. The hose connections between the fermenter and the filtration unit, including the pump hose, had previously been sterilized by autoclaving and the filtration system had previously been sterilized by means of water vapor flowing through it (1.2 bars superpressure, 30 minutes).

The concentrated biomass in the reactor was washed by diafiltration with 2 liters of sterile mineral salt solution (cf. example 1) and then the fermenter was filled with induction medium. The induction medium was composed as follows:

| N-acetyldehydroleucine | 25 g/l |
|---|---|
| Yeast extract | 35 g/l |
| Mineral salt solution | 4.5 l |
| pH | 6.5 |

The conditions for enzyme induction were:

| pH | 6.5 |
|---|---|
| Temperature | 31.5° C. |
| Concentration of the dissolved oxygen (% saturation) | 80% |
| Maximum agitator speed | 300 rpms |

Specimens were taken at different times and the maximum attainable enzyme content and the best harvesting time determined after turbidimetric measurement (optical density at 660 nM) and a test for acylase activity. The acylase tests were prepared with 0.02 M N-acetyldehydroleucine in 0.1 M glycine/sodium hydroxide buffer, pH 10, and carried out as described in Example 1.

It was found that the acylase is formed only during the 2nd fermentation phase and the enzyme activity reaches its maximum value approximately 24 hours after the addition of the induction medium.

b) Recovery of the raw extract

The moist bacterial mass (133 g) was suspended in 50 mM glycine buffer, pH 11, so that the concentration of the cellular suspension was 40 % (final volume 333 ml). The cell contents were released in the cooled suspension (approximately 4°0 C.) by means of a mechanical cellular digestion in a glass bead mill (Bachofen—Dyno-Mill, type KLD). The grinding container, comprising 680 ml, was filled with glass beads 0.3 mm in size, so that a bulk volume of 578 ml resulted (85%). The digestion was carried out at an agitator-shaft speed of 3000 rpms while the cooling jacket of the grinding container as well as the agitator shaft bearing were cooled during running with ethylene glycol solution of −20° C. in order to largely avoid a heating of the product. After 4 minutes digestion time, a degree of disintegration of over 90% was achieved. The glass beads were separated by means of 2 minutes centrifugation at 3000 g, washed twice by mixing them each time with 192 ml glycine buffer and were centrifuged off again. The supernatants of the centrifugation steps were combined and the greater part of the cell fragments separated by means of 30 minutes centrifugation at 12000 g in a refrigerated centrifuge. It was found that the raw extract, compounded to 50% (w/v) with glycerin, could be stored at −20° C. for months without loss of activity.

EXAMPLE 3

Growth of Zoogloea ramigera ABI 1 a) Growth at various start pH'es

The pH was varied from 6.5—10 in stages of 0.5 units in a medium consisting of mineral salt solution (cf. Example 1) and 7 g/l yeast extract. Specimens were taken at different times from the cultures (30 ml in 100 ml Erlenmeyer flasks) incubated on a rotary agitator machine at 110 rpms at 30° C. in which specimens the bacterial mass was determined by measuring the optical density at 660 nm.

After 43 hours of growth, the highest cell density was reached in a pH range between 8 and 8.5 b) Growth at different yeast extract concentrations

The growth of strain ABI 1 was followed in agitated cultures (as described under a)) with a medium of mineral salt solution (cf. Example 1) and 7-25 g/l yeast extract with an initial pH of 8.25 by measuring the optical density at 660 nm.

It was found that the rate of microorganism growth is retarded when the yeast extract concentration is 15 g/l or more.

EXAMPLE 4

Induction of N-acetyldehydroleucine acylase a) Changing of the inductor

Different substances were added in a concentration of 3 g/l as inductors into agitated cultures with a medium of mineral salt solution (cf. Example 1) with 0.5 g/l yeast extract and 0.5 g/l peptone at pH 7. The technology for agitated cultures is described in Example 1 a).

As can be seen from Table 2, N-acetyldehydroleucine exhibits the highest induction capacity. N-acetylamino acids or 2-acetylamino cinnamic acid are only slightly active.

TABLE 2

| Acylase activity after 60 hours of incubation as a function of the inductor | | | |
|---|---|---|---|
| Inductor | U/mg | Inductor | U/mg |
| AD-leucine | 0.222 | Ac-L-leucine | 0.018 |
| AD-isoleucine | 0.172 | Ac-D,L-tryptophan | 0.018 |
| AD-valine | 0.121 | 2-Acetylamino-cinnamic acid | 0.016 |
| Ac-L-isoleucine | 0.039 | | |
| Ac-D,L-valine | 0.031 | Ac-D,L-tyrosine | 0.011 |
| Ac-D,L-phenyl-alanine | 0.031 | Control | 0.015 |

AD: N-acetyldehydro-
AC: N-acetylb) Variation of the starting pH

The pH was varied from 5.5-9 in stages of 0.5 units in the mineral salt medium with 3 g/l N-acetyldehydroleucine and 2 g/l yeast extract.

The enzyme production reaches its optimum at pH 6.5 and drops sharply as the pH increases, as is shown in Table 3.

TABLE 3

| Relationship between the acylase formation by means of strain ABI 1 and the pH | | |
|---|---|---|
| pH | U/mg | U/l |
| 5.5 | * | * |
| 6.0 | * | * |
| 6.5 | 0.202 | 14.6 |
| 7.0 | 0.136 | 13.3 |
| 7.5 | 0.115 | 10.8 |
| 8.0 | 0.075 | 7.6 |
| 8.5 | 0.069 | 5.3 |
| 9.0 | 0.064 | 5.3 | c) Varying the concentration of N-acetyldehydroleucine

Zoogloea ABI 1 was cultivated in a mineral salt medium with start pH 8 and 7 g/l yeast extract at 30° C. with a rotary agitator machine. After 48 hours, the cells were centrifuged for 10 minutes at 8000 g, resuspended in the above-mentioned medium with different concentrations of N-acetyldehydroleucine and a pH of 6.5 and incubated for a further 16 hours in a rotary agitator.

Table 4 shows that no further increase of the enzyme production can be detected above 5 g/l N-acetyldehydroleucine.

TABLE 4

| Acylase activity as a function of the N-acetyldehydroleucine concentration in a two-stage agitated culture | | |
|---|---|---|
| N-acetyldehydroleucine (g/l) | Acylase production | |
| | U/mg | U/l |
| control | 0.015 | 5 |
| 3 | 0.140 | 41 |
| 5 | 0.189 | 70 |
| 7 | 0.190 | 65 |
| 9 | 0.204 | 72 |

EXAMPLE 5

Purification of the Acylase a) Precipitation of nucleic acids with polyethylene imine A raw extract (666 ml) was obtained by means of fermentation, cellular digestion in a glass bead mill and centrifugation. The extract was cooled in an ice bath and combined with 35 ml of a 10% polyethylene imine solution (rel. molecular mass 30–40·$10^3$) with a pH of 11 and incubated 5 minutes at 0° C. The precipitated nucleic acids, as well as cell fragments not yet separated out, were sedimentated by means of 30 minutes centrifugation in a refrigerated centrifuge at 18000 g.

It was possible to incrfeatene the yield by 18.6 % and the enrichment factor by 206 % by means of the nucleic acid precipitation in the subsequent ammonium sulfate fractionation.

b) Protein precipitation with ammonium sulfate

The supernatant (690 ml) was compounded with 460 ml of a saturated ammonium sulfate solution (761 g/l) whose pH had been adjusted by the addition of solid sodium hydroxide to 9 and was agitated 30 minutes in an ice bath. The precipitated protein was sedimentated 30 minutes at 15000 g in a refrigerated centrifuge and dissolved in 200 ml 50 mM glycine buffer with a pH of 11.

c) Salting-out chromatography on sepharose CL-4B

The concentrated dissolved protein precipitate was treated by adding ammonium sulfate solution until a conductivity of 80–90 mS/cm had been achieved, which corresponds at pH 11 to an ammonium sulfate concentration of approximately 25% saturation. Precipitated protein was centrifuged off at 15000 g (30 minutes). 125 ml of the supernatant (250 ml in toto) were applied onto a sepharose CL-4B column (2.6-22.6) which had been equilibrated with 25% ammonium sulfate (pH 11). The elution took place by establishing a gradient (500 ml) decreasing from 26 to 0%. The eluate was trapped in fractions of 5 ml. The acylase desorbed at 17-19% ammonium sulfate saturation from the chromatography gel. The active fractions (25 ml) were combined and diluted with saturated ammonium sulfate solution (pH 9) to the double volume. After 30 minutes incubation in an ice bath, the precipitated protein was centrifuged off and taken up in 2 ml 50 mM glycine buffer with pH 11. The concentrated acylase preparation was compounded to 43.5% (w/v) with glycerin and stored at −20° C.

Since only 10–17% of the applied protein bonds to the column in the chromatographic process described here, it is possible to work up large amounts of protein with a relatively small column.

d) Analytical fast protein liquid chromatography (FPLC) on Mono-Q 0.255 ml of the concentrated acylase preparation compounded with glycerin was diluted with 1.13% (v/v) Triton X-100 in 50 mM glycine buffer (pH 11) to 2 ml and applied onto the Mono-Q column (1 ml), which had been equilibrated with the above-mentioned glycine buffer supplemented with 0.2% Triton X-100. Elution was carried out with a $Na_2SO_4$ gradient (40 ml) rising from 0 to 0.15 M while the acylase was washed at 0.047–0.050 M $Na_2SO_4$ from the column. After the active fractions had been combined, the purified enzyme was partially compounded with 43.5% (w/v) glycerin for storage at −20° C. and partially glycerinated to 25% (w/v) for preservation at 4°–8° C. in a refrigerator. No activity loss could be recorded under the latter conditions after 76 days. Table 5 shows the results of the purification.

TABLE 5

Purification scheme for N-acetyldehydroleucine acylase

| Specimen/ purification step | Total Enzyme (U) | Yield (%) | Specific Activity (U/mg) | Enrichment Factor |
|---|---|---|---|---|
| Raw extract | 1963 | 100 | 0.348 | 1 |
| Nucleic acid precipitation (0.9% PEI) | 1810 | 92 | 0.376 | 1.08 |
| Ammonium sulfate precipitation (0–40%) | 1505 | 77 | 1.27 | 3.65 |
| Salting-out chromatogr. (26–0% ammonium sulfate) | 785 | 40 | 12.0 | 34.5 |
| Concentrating (precipitation with 60% ammonium sulfate) | 785 | 40 | 13.3 | 38.2 |
| FPLC-Mono-Q (0–0.15 M sodium sulfate in 0.2% Triton X-100) | 557 | 28 | 74–109 | 213–313 |

PEI: Polyethylene imine, rel. molecular mass: $30 - 40 \cdot 10^3$

EXAMPLE 6

Effect of pH on the reaction rate

The reaction rate of the hydrolytic splitting of acetic acid from the compound N-acetyldehydroleucine in the presence of the ADL acylase was determined as a function of the pH in the reaction mixture. The test batch was composed as follows:

| | |
|---|---|
| 200 mM N-acetyldehydroleucine in 20 mM tris/ phosphoric acid buffer (pH 9) | 0.05 ml |
| 1.0 U/ml acylase | 0.01 ml |
| 0.1 M buffer | 0.44 ml |

Before the reaction batches were mixed together, different pH values in the range of 5 to 7.5 in the potassium phosphate buffer, 7.5 to 9 in the tris buffer and 7 to 12 in the glycine buffer were adjusted by means of the addition of sodium hydroxide and phosphoric acid. The pH values present under test conditions were measured in reference batches without enzyme. After 10 minutes reaction time at 30° C., the enzyme activities were determined by means of colorimetric measuring of the keto acid concentration (cf. Example 1).

The optimum for the reaction rate in the glycine buffer is in a pH range between 8.6 and 10.1, in the glycine-free buffers between 7.7 and 9.1.

EXAMPLE 7

Optimum reaction temperature

Test batches with 20 mM N-acetyldehydroleucine in 0.1 M glycine buffer (pH 9) were pretempered 5 minutes at temperatures between 10° and 70° C. and then the enzyme reaction was started by means of the addition of acylase. At temperatures of 10° to 40° C., the batches contained 0.0666 U/ml enzyme, at 40° to 70° C. 0.02 U/ml. After 2 minutes, the enzyme reactions were stopped by means of the addition of ice-cooled analytical reagent, the test tubes cooled down in an ice bath and, after 15 minutes incubation at 30° C., alkalized as is customary for color development (cf. Example 1).

The maximum reaction rate is reached at 55° C. and is greater by a factor of 3.1 than at the standard temperature of 30° C.

EXAMPLE 8

Stability of the N-acetyldehydroleucine acylase a) pH stability

The pH stability of the ADL acylase was investigated in the pH range of 7 to 12. Enzyme purified on Mono-Q was diluted 20-fold with various buffers of differing pH values and stored for 3 weeks at 25° C. Specimens were taken at various times and their enzyme activities were tested under standard conditions. The following buffers were used for the different values:

| | |
|---|---|
| 0.1 M potassium phosphate | pH 7.0, 7.5 |
| 0.1 M tris/phosphoric acid | pH 7.5, 8.0, 8.5, 9.0 |
| 0.1 M glycine | pH 9.0, 9.5, 10.0, 10.5, 11.0, 11.5, 12.0 |

The mixing together of the batches, their storage and the taking of specimens took place under sterile conditions. The standard conditions for the enzyme test were:
20 mM N-Acetyldehydroleucine
Acylase in a limiting amount so that the linearity range of the subsequent color test (cf. Example 1) was not exceeded
0.1 M glycine buffer
pH 9

As is apparent in Table 6, approximately 30–40% of the original acylase activity was still detectable in the pH range of 9–10.5 after 3 weeks.

TABLE 6 pH stability of the A-acetyldehydroleucine acylase

| Buffer pH | Residual activity (%) after | | | | |
|---|---|---|---|---|---|
| | 1 day | 3 days | 1 week | 2 weeks | 3 weeks |
| Potassium phosphate (0.1 M) | | | | | |
| 7.0 | 78 | 16 | 0 | 0 | 0 |
| 7.5 | 83 | 39 | 0 | 0 | 0 |
| Tris/phosphoric acid (0.1 M) | | | | | |
| 7.5 | 61 | 37 | 0 | 0 | 0 |
| 8.0 | 60 | 44 | 7 | 0 | 0 |
| 8.5 | 63 | 62 | 37 | 13 | 9 |
| 9.0 | 92 | 80 | 56 | 25 | 27 |

TABLE 6-continued

| pH stability of the A-acetyldehydroleucine acylase | | | | | |
|---|---|---|---|---|---|
| Buffer | Residual activity (%) after | | | | |
| pH | 1 day | 3 days | 1 week | 2 weeks | 3 weeks |
| Glycine (0.1 M) | | | | | |
| 9.0 | 97 | 91 | 64 | 35 | 30 |
| 9.5 | 89 | 103 | 68 | 35 | 37 |
| 10.0 | 102 | 99 | 68 | 34 | 43 |
| 10.5 | 98 | 95 | 57 | 28 | 25 |
| 11.0 | 86 | 86 | 54 | 15 | 7 |
| 11.5 | 71 | 69 | 35 | 5 | 2 |
| 12.0 | 4 | 3 | 0 | 0 | 0 | b) Temperature resistance of the acylase

The acylase was incubated 30 minutes at temperatures of 10° to 70° C. and then the activity test was carried out under standard conditions (cf. Example 8a)). After 30 minutes at 50° C., 89% of the initial activity can still be demonstrated, at higher temperatures the acylase is rapidly deactivated.

c) Stability of the acylase in the presence of different anions

The influence of different anions on the stability of ADL acylase was investigated. Raw extract which had been compounded with glycerin to 43.5% (w/v) was diluted 1 : 10 with 0.5 molar solutions of various sodium salts in 50 mM glycine (pH 11) and stored at room temperature (20° to 25° C.). Specimens were taken from time-to-time and their enzymatic activity measured under standard conditions, as described in Example 8a).

It was found that the stability of the acylase increases with the charge and the size of the anion (cf. Table 7).

TABLE 7

| Stability of N-acetyldehydroleucine acylase in the presence of various sodium salts | | | |
|---|---|---|---|
| Sodium salt | % Residual activity after | | |
| (0.5 M) | 3 days | 6 days | 21 days |
| Phosphate | 96 | 105 | 27 |
| Sulfate | 89 | 94 | 15 |
| Acetate | 86 | 81 | 6 |
| Formate | 76 | 63 | 2 |
| Chloride | 35 | 0 | 0 |

EXAMPLE 11

Influences of inhibitors and activators a) Influence of chelating agents, metal cations and enzyme inhibitors The influence of various additive substances on the reaction rate of the splitting of N-acetyldehydroleucine was measured under standard conditions, as described in Example 8a).

It can be seen from Table 8 that only inhibitors of serine hydrolases sharply inhibit the acylase, especially phenylmethane sulfonyl fluoride still in micromolar concentration.

TABLE 8

| Influence of additive substances on the N-acetyldehydroleucine acylase activity | | | |
|---|---|---|---|
| | % Residual activity | | |
| Inhibitor | 1 mM | 10 mM | 100 mM |
| Complexing agents: | | | |
| EDTA | * | 95 | * |
| Citrate | 99 | 84 | * |
| Bipyridine | 91 | 70 | * |

TABLE 8-continued

| Influence of additive substances on the N-acetyldehydroleucine acylase activity | | | |
|---|---|---|---|
| | % Residual activity | | |
| Inhibitor | 1 mM | 10 mM | 100 mM |
| Phenanthroline | 94 | 52 | * |
| NaN$_3$ | 105 | 103 | * |
| Bivalent Cations: | | | |
| CaCl$_2$ | * | 93 | * |
| CuSO$_4$ | 87 | 83 | * |
| CoCl$_2$ | 91 | 85 | * |
| MgCl$_2$ | 95 | 88 | * |
| MnCl$_2$ | 99 | 87 | * |
| ZnCl$_2$ | 95 | 82 | * |
| Reducing agents: | | | |
| MeSH | 93 | 99 | 81 |
| Glutathione reduced | 95 | 95 | * |
| Dithiothreitol | 103 | 58 | * |
| SH Group reagents: | | | |
| pCMB | 104 | 98 | * |
| pOHMB | 93 | 91 | * |
| iodine acetamide | 104 | 74 | * |
| iodine acetate | 76 | 49 | * |
| HgCl$_2$ | 84 | 70 | * |
| KCN | 105 | * | * |
| Inhibitors of PLP enzymes: | | | |
| Cycloserine | 111 | 105 | * |
| Semicarbazide | 113 | 93 | * |
| Inhibitors of serine hydrolases | | | |
| Neostigmine | 102 | 82 | 0 |
| pABA**) | * | 89 | 54 |
| PMSF | 0.0001 mM: 10 | 0.01 mM: 0 | * |

*defined above as "not determined, as growth too slight".]
**)pABA to 200 mM: 0% residual activity
MeSH: mercaptoethanol
pABA: para-aminobenzamidine
pCMB: para-hydroxy mercury benzoate PLP: pyridoxal phosphate
pOHMB: para-hydroxy mercuric benzoate
PLP: Pyridoxyl phosphate
PMSF: phenylmethane sulfonyl fluoride b) Influence of glycine on the reaction rate The reaction of glycine in 0 to 1.2 molar concentration dissolved in 0.1 M tris/HCl buffer was determined under standard conditions (example 8a).

Glycine accelerates the splitting of N-acetyldehydroleucine by the ADL acylase a maximum of 3.3 times. The glycine concentration which is necessary for one-half the maximum reaction acceleration is 90 mM (calculation according to T. Ingami and T. Murachi, J. Biol. Chem. 238 (5), pp. 1905–1907, 1963).

EXAMPLE 12

Determination of the molecular weight and of the number of subunits

The molecular weight of the native enzyme was determined by means of gel filtration on sephacryl S-200 HR. The column (1.6×69.6 cm), coupled to a FPLC system, was operated with a flowthrough rate of 1 ml/minute and 0.1 ml of the enzyme which was glycerinated and purified by means of salting-out chromatography served as specimen after a twofold dilution. The following served as reference proteins: Cytochrom C (horse), myoglobin (whale), myoglobin (horse), aldolase (rabbit muscle), carboanhydrase and bovine serum albumin. The molecular weight of the acylase is 65,000±5000.

A molecular weight of 55,000±4000 was determined in gel electrophoresis in the presence of sodium dodecylsulfate (SDS) for the denatured enzyme. Accordingly, the acylase consists of a polypeptide chain of an unusual length. The following were used for the calibration curve: $\alpha_2$-macroglobulin (equine plasma), phosphorylase b (rabbit muscle), glutamate dehydrogenase (bovine liver), lactate dehydrogenase (swine muscle) and trypsin inhibitor (soy bean).

EXAMPLE 13

Substrate specificity of N-acetyldehydroleucine acylase a) Dependency of the acylase activity on the concentration of various N-acetyldehydroamino acids The activity of the acylase was determined under standard conditions (cf. Example 8a)) with various N-acetyldehydroamino acids in concentrations of 0.1 to 300 mM. A second series of measurements with N-acetyldehydroleucine in the above-indicated concentration range was placed in 0.1 M tris/phosphoric acid buffer.

The $K_M$ value for ADL is 4.5 mM in glycine buffer. The kinetic data for the splitting of the acetyldehydroamino acids is collated in Table 9.

TABLE 9

Kinetic data of N-acetyldehydroleucine acylase

| Substrate | Buffer | % $V_{max}$ | $K_M$ (mM) | $K_I$ (mM) |
|---|---|---|---|---|
| ADL | glycine, 0.1 M | 100 | 4.53 | 418 |
| ADI | glycine, 0.1 M | 14 | 5.77 | 140 |
| ADV | glycine, 0.1 M | 23 | 20.9 | 732 |
| ACA | glycine, 0.1 M | 46 | 2.62 | 942 |
| ADA | glycine, 0.1 M | 90 | 6.68 | 714 |
| ADL | tris-phosphoric acid 0.1 M | 62 | 7.01 | 2564 |

Reaction conditions: 0.1 M glycine, pH 9, 30° C.
Adaptation to the equation $v = V_{max} \cdot S/(K_M + S + S^2/K_I)$ (W. Cleland, 1963, Methods in Enzymology 63, pp. 103-138).
ADL: acetyldehydroleucine
ADI: acetyldehydroisoleucine
ADV: acetyldehydrovaline
ACA: acetylamino cinnamic acid
ADA: acetyldehydroalanine (= N-acetylamino acrylic acid).

b) Hydrolysis of other compounds by N-acetyldehydroleucine acylase

A qualitative check was performed for 81 compounds to see whether they are accepted as substrate by the acylase. The test batches contained:
50 mM test substrate
0.343 U/ml acylase
0.1 M tris/HCl buffer
pH 9

After 16 and 40 hours incubation at 25° C., specimens were taken from the batches, most of which specimens were analyzed in comparison to substrate standards by means of thin-layer chromatography (70% (v/v) ethanol as mobile solvent). The detection took place with ninhydrin spray reagent. A few specimens were tested in addition or alternatively with the amino acid analyzer.

The test batches for the hydrolysis of hydantoins had the following composition:
25 mM substrate or buffer
1 U/ml acylase
50 mM tris/phosphoric acid buffer
pH 9
total volume 100 μl Isopropylhydantoin, hydantoic acid and dihydrouracil were used as substrates. After 11.5 hours at 30° C., 175 μl 12% (w/v) trichloroacetic acid and 25 μl analytical reagent (10 % (w/v) p-aminobenzaldehyde in 6 N HCl) were added, precipitated protein centrifuged off in an Eppendorf table centrifuge and the absorption in the supernatants measured at 450 nm.

In order to determine the enzymatic hydrolysis rate of 4-nitrophenylacetate, the rate of increase in extinction of the liberated 4-nitrophenol (402 nm) was measured for the following batch:
20 mM 4-nitrophenylacetate
0.2 U/ml acylase
0.1 M potassium phosphate buffer
pH 7
25° C.

In order to take the chemical hydrolysis into account, the extinction increase rate in a batch without acylase was deducted from the value determined in this manner. The enzyme activity was calculated using a straight calibration line with 4-nitrophenylacetate.

The amino acids produced from the amino acid amides by means of the action of acylase were detected quantitatively with the amino acid analyzer.

For the determination of the relative activities, the hydrolysis rate with N-acetyldehydroleucine under comparable reaction conditions was equated with 100%.

Only tryptophane amide is split with a reaction rate on the order like that achieved with N-acetyldehydroamino acids (cf. Table 10).

TABLE 10

Substrate specificity of N-acetyldehydroleucine acylase

| Substrate | rel. activity (%) |
|---|---|
| ADL | 100.0 |
| L-tryptophane amide | 20.4 |
| L-leucine amide | 6.80 |
| D-leucine amide | 3.82 |
| L-methionine amide | 4.69 |
| L-alanine amide | 0.35 |
| D-alanine amide | 0.46 |
| 4-nitrophenylacetate | 1.1 |
| N-acetyl glycine | 0 |
| L-tryptophyl glycine | 0 |
| L-leucyl glycine | 0 |
| L-alanyl glycine | 0 |
| Glycyl-L-leucine | 0 |
| L-alanyl-L-leucine | 0 |
| N-acetyl-L-alanyl-L-valine | 0 |
| L-alanyl-L-phenylalanine amide | 0 |
| N-acetyl-D,L-leucine | 0 |
| N-acetyl-L-phenylalanine | 0 |
| N-benzoyl-D,L-leucine | 0 |
| N-methoxycarbonyl-D,L-leucine | 0 |
| N-methoxycarbonyl-D,L-valine | 0 |
| N-methyl-D,L-leucine | 0 |
| N-methyl-L-glutamic acid | 0 |
| N-carbamoyl-L-valine | 0 |
| N-carbamoyl-L-phenylalanine | 0 |
| Isopropy hydantoin | 0 |
| Dihydrouracil | 0 |

EXAMPLE 14

Continuous preparation of L-leucine N-acetyldehydroleucine can be converted enzymatically to L-leucine by reductively aminating the intermediate 2-keto isocaproate stereospecifically by means of coupling the acylase with an L-leucine dehydrogenase. The regeneration of the coenzyme oxidized in the dehydrogenation reaction took place in the presence of formate by means of a formate dehydrogenase. The reaction was carried out continuously in an enzyme membrane reactor. The latter contained, at the start of the experiment:
6.63 U/ml Acylase (prepared with 75 U/ml from the salting-out chromatography)

11.2 U/ml L-leucine dehydrogenase (*Bacillus cereus*)
8.4 U/ml formate dehydrogenase (*Candida boidinii*)
0.6 mM PEG 20000-NADH (prepared according to German Patent DE-PS 2,818,414)
900 mM ammonium formate (pH 9).

The reactor contents (10 ml), tempered to 25° C., were pumped by a hose pump in a circuit via an ultrafiltration membrane (type YM5, company Amicon, exclusion limit 5000 Daltons). The low-molecular substances can be continuously removed by this means, whereas the enzymes and the coenzyme, which is increased in molecular weight, are retained in the reaction solution. The volume of the ultrafiltered product solution, approximately 9 ml/hour, was continuously replaced with substrate solution. The average dwell time was accordingly 1.1 hours. The substrate solution contained 50 mM N-acetyldehydroleucine in the first 53 operating hours and 75 mM in the following 57 hours, dissolved in each instance in 900 mM ammonium formate with pH 9. The product solution was collected in fractions and its L-leucine concentration determined by means of an enzymatic test with L-leucine dehydrogenase according to the end-point method. The test batches contained:
10% (v/v) specimen or standard with a maximum of 2 mM L-leucine
3.4 mM NAD+
4.8 U/ml L-leucine dehydrogenase
80 mM glycine buffer, pH 10.7

The extinction (340 nm) was measured in the batches prior to the start of the reaction, by means of the addition of enzyme, as well as after 90 minutes incubation at room temperature, and an L-leucine concentration determined from the difference using a calibration curve.

Table 11 shows that it is possible to convert N-acetyl-dehydroleucine to L-leucine in a continuous manner with a high yield.

TABLE 11

| Continuous preparation of L-leucine from N-acetyldehydroleucine | | | |
|---|---|---|---|
| Time interval (h) | N-acetyldehydro-leucine (mM) | Yield of L-leucine*) (%) | Conversion (%) |
| 0-53 | 50 | 90 | 91 |
| 53-110 | 75 | 84 | 86 |

*)average values in time

EXAMPLE 15

Preparation of L-tryptophyl glycine from L-tryptophane amide and glycine a) pH optimum of the L-tryptophyl glycine syntheses It is possible to prepare L-tryptophyl glycine (O-Trp-Gly) from L-tryptophane amide (L-Trp-$NH_2$) and glycine by the action of ADL acylase. L-tryptophane (L-Trp) and ammonia are produced as byproducts. Different pH values between 7 and 11 were adjusted in batches consisting of
50 mM L-Trp-$NH_2$
200 mM glycine
2.6 U/ml ADL acylase
100 mM buffer at pH 7-9
by means of the addition of sodium hydroxide solution and phosphoric acid. Potassium phosphate was used as buffer substance at pH 7 and tris/phosphoric acid at pH 8 and 9. After 18 hours incubation at 25° C., the composition of the specimens was investigated in comparison to standard solutions by means of thin-layer chromatography. The mobile solvents used were glacial acetic acid/butanol/water in a volumetric ration of 2/8/2 as well as methylethylketone/pyridine/water/glacial acetic acid in a ratio of 70/15/15/2. The detection took place in the case of the first-named mobile solvent via UV quenching of fluorescence at 254 nm as well with the ninhydrin spray reagent and in the case of the latter mobile solvent only with the ninhydrin method. The concentrations of L-Trp and L-Trp-Gly were determined using standards on an amino acid analyzer.

As can be seen from Table 12, the optimum of the synthesis reaction is at pH 10. At this pH, 94% of the L-Trp-$NH_2$ added is split and 64% thereof converted to the dipeptide (64% selectivity).

TABLE 12

| Influence of the pH on the synthesis of L-tryptophyl glycine | | | |
|---|---|---|---|
| pH | Dipeptide yield (%) | Selectivity (%) | Conversion (%) |
| 7 | 10 | 10 | 100 |
| 8 | 25 | 25 | 100 |
| 9 | 44 | 45 | 98 |
| 9.5 | 53 | 57 | 92 |
| 10 | 60 | 64 | 94 |
| 10.5 | 53 | 63 | 84 |
| 11 | 45 | 62 | 73 | b) Influence of the L-Trp-$NH_2$ concentration on the L-Ltp-Gly syntheses

The L-Trp-$NH_2$ concentration of 24.4 to 400 mM was varied in batches for the synthesis of L-Trp-Gly from L-Trp-$NH_2$ and glycine in the presence of ADL acylase (purified via salting-out chromatography). Glycine was added in a 400–488 molar excess to the L-Trp-$NH_2$ and the acylase concentration raised in proportion to that of the L-Trp-$NH_2$ (3.6 U/ml per 50 mM L-Trp-$NH_2$). Incubation and evaluation took place as described in a).

In the range from 24 to 182 mM, over 50% of the L-Trp-$NH_2$ is converted to the dipeptide (cf. Table 13).

TABLE 13

| Synthesis of L-Trp-Gly as a function of the L-Trp-$NH_2$ concentration | | | |
|---|---|---|---|
| L-Trp-$NH_2$ (mM)· | Yield (%) | Selectivity (%) | Conversion (%) |
| 24.4 | 51 | 72 | 71 |
| 47.6 | 59 | 66 | 89 |
| 95.2 | 59 | 59 | 100 |
| 140 | 55 | 56 | 97 |
| 182 | 51 | 54 | 94 |
| 298 | 36 | 56 | 63 |
| 400 | 12 | 53 | 22 | c) Influence of polar substances in the reaction mixture on L-Trp-Gly synthesis

Batches for L-Trp-Gly synthesis from L-Trp-$NH_2$ (50 mM) and glycine (500 mM, pH 10) in the presence of ADL acylase were compounded with various ionic and uncharged polar compounds in a high concentration and incubated 19 hours at 25° C. The acylase was partially purified by means of salting-out chromatography at 2.6 U/ml and used as pure enzyme after chromatography on Mono-Q at 1.5 U/ml. Thereafter, the content of tryptophane compounds in the reaction mixtures was determined as described in a).

Table 14 shows that at 50% (w/v) glycerin, a selectivity which is greater by 12% points is achieved with the same yield as in the reference batch.

TABLE 14

Influence of ionic and uncharged polar substances on the L-Trp-Gly synthesis

| Substance | Concentration (% w/v) | Selectivity (%) | Yield (%) | Conversion (%) |
|---|---|---|---|---|
| Partially purified Acylase: | | | | |
| Control | — | 67 | 64 | 96 |
| Potassium phosphate | 5.0 | 59 | 59 | 100 |
| Potassium phosphate | 10.0 | 48 | 48 | 100 |
| Ammonium sulfate | 12.5[a] | 65 | 65 | 100 |
| Ammonium sulfate | 25.0[a] | 63 | 68 | 89 |
| Ethanol | 10.0[b] | 66 | 66 | 100 |
| " | 20.0[b] | 72 | 64 | 89 |
| Glycerin | 25.0 | 71 | 71 | 100 |
| " | 50.0 | 79 | 65 | 83 |
| Pure acylase: | | | | |
| Control | — | 73 | 62 | 85 |
| glycerine | 25 | 78 | 56 | 72 |
| " | 50 | 83 | 54 | 66 |

[a] % saturation
[b] % v/v

EXAMPLE 16

Preparation of L-Trp-dipeptides from L-Trp-NH$_2$ and D- and L-amino acids

An investigation was made as to whether D- and L-amino acids can also function instead of glycine as amino components for the dipeptide synthesis form L-Trp-NH$_2$ in the presence of ADL acylase. The D- and L-amino acids were used close to their solubility limit or at a maximum of 0.5 M in tests with the following composition:
100–500 mM D- or L- amino acid
50 mM L-Trp-NH$_2$
2.6 U/ml acylase (purified by means of salting-out chromatography)
pH 10.

The batches were incubated for 19 hours at 25° C. and then tested with an amino acid analyzer and by thin-layer chromatography for their content of ninhydrin-positive compounds (mobile solvent methylethylketone/pyridine/water/glacial acetic acid in a ratio of 70/15/15/2. Amino acids as well as the dipeptides L-Trp-Gly, L-Trp-D,L-alanine and L-Trp-D,Lphenylalanine were identified in comparison to standard solutions and quantified. Additional peaks in the remaining analyzer chromatograms were also interpreted analogously as dipeptides and their concentration estimated using the average specific peak area of above-named standard solutions (+10% standard deviation).

As is apparent from Table 15, approximately 40% and 15% of the L-Trp-NH$_2$ is converted to the corresponding dipeptide with the amino acids D-methionine and D-cysteine.

TABLE 15

D- and L-amino acids as amino components for the synthesis of tryptophyl dipeptides

| Amino components | Conc. (mM) | Yield (%) | Conversion (%) | Selectivity (%) | Type of calculation |
|---|---|---|---|---|---|
| Glycine | 500 | 66 | 100 | 66 | * |
| D-methionine | 300 | 39 | 99 | 40 | ** |
| D-leucine | 150 | 23 | 100 | 23 | ** |
| L-methionine | 300 | 22 | 95 | 22 | ** |
| D-alanine | 500 | 22 | 87 | 26 | * |
| D-cysteine | 500 | 15 | 85 | 17 | ** |
| L-alanine | 500 | 12 | 99 | 12 | * |
| D-valine | 500 | 12 | 91 | 13 | ** |
| D-phenylalanine | 150 | 11 | 59 | 18 | * |
| D-serine | 500 | 10 | 100 | 10 | ** |
| L-cysteine | 500 | 3 | 94 | 3 | ** |
| L-leucine | 150 | 0 | 100 | 0 | — |
| L-valine | 500 | 0 | 93 | 0 | — |
| L-phenylalanine | 150 | 0 | 100 | 0 | — |
| D-tryptophane | 100 | 0 | 100 | 0 | — |
| L-tryptophane | 100 | 0 | 100 | 0 | — |
| D-histidine | 150 | 0 | 83 | 0 | — |
| L-histidine | 150 | 0 | 91 | 0 | — |
| D-proline | 500 | 0 | 100 | 0 | — |
| L-proline | 500 | 0 | 100 | 0 | — |
| L-lysine | 500 | 0 | 100 | 0 | — |
| L-arginine | 150 | 0 | 100 | 0 | — |
| L-glutamic acid | 500 | 0 | 77 | 0 | — |

*Using it's own calibration standard
**average standard from calibrations with 4 tryptophyl dipeptides (see above)

EXAMPLE 17

Enantioselectivity of the tryptophyl dipeptide synthesis with N-acetyldehydroleucine acylase The stereospecificity of ADL acylase in the synthesis of dipeptides was investigated as regards the carboxyl component Trp-NH$_2$ and the amino component methionine. The batches described in the following were incubated 25 hours at 25° C.
50 mM L- or D,L-Trp-NH$_2$
300 mM D- or L-methionine or 500 mM glycine
2.6 U/ml acylase
pH 10

The concentrations of amino acid and of dipeptide were determined as described in Example 16.

The acylase prefers the L enantiomer of Trp-NH2 as carboxyl component and the D form of methionine as amino component (cf. Table 16).

TABLE 16

Dipeptide synthesis as a function of the stereoconfiguration of the starting materials

| Trp-NH$_2$ Stereo Config. | Amino-component/ Conc. (mM) | Dipeptide | t$_r$ min | Yield (%) | Conv. (%) | Selectivity (%) |
|---|---|---|---|---|---|---|
| L | Gly/500 | L-Trp-Gly | 49.77 | 65 | 100 | 65 |
| D,L | Gly/500 | D,L-Trp-Gly | 49.79 | 60 | 100 | 60 |
| L | L-Met/300 | L-Trp-L-Met | 49.31 | 25 | 97 | 26 |
| L | D-Met/300 | L-Trp-D-Met | 49.92 | 50 | 100 | 50 |
| D,L | L-Met/300 | L-Trp-L-Met | 49.29 | 15 | 84 | 19 |
| D,L | D-Met/300 | L-Trp-D-Met | 49.87 | 44 | 93*) | 48*) |
| | | D-Trp-D-Met | 49.33 | 39 | 93*) | 42*) |

TABLE 16-continued

Dipeptide synthesis as a function of the stereoconfiguration of the starting materials

| Trp-NH$_2$ Stereo Config. | Amino-component/ Conc. (mM) | Dipeptide | t$_r$ min | Yield (%) | Conv. (%) | Selectivity (%) |
|---|---|---|---|---|---|---|
| | | Average | | 42 | 93 | 45 |

*)assuming the same conversion of both antipodes of the Trp-NH$_2$
Gly: glycine
Met: methionine
t$_r$ = retention time

What is claimed is:

1. An isolated microbiologically produces N-acetyl-2,3-didehydroleucine acylase, having the following properties:

a) reactivity:
said acylase splits off the acetyl group from N-acetyl-2,3-didehydroleucine, resulting in acetic acid and 2,3-didehydroleucine, the latter hydrolyzing to NH$_3$ and 2-keto-4-methylvaleric acid;

b) substrate specificity;
said acylase hydrolyses both N-acetyl-2,3-didehydroamino acids comprising N-acetyl-2,3-didehydrovaline, N-acetyl-2,3-didehydroisoleucine, 2-acetylamino cinnamic acid and 2-acetylamino acrylic acid as well as amino acid amides such as D- and L-tryptophane amide, D- and L-leucine amide and L-methionine amide but not 2,3-saturated N-acetylamino carboxylic acids such as N-acetyl leucine or N-acetyl valine;

c) optimum pH:
the optimum pH is 9.3±1;

d) pH stability: It exhibits good stability in a pH range between 9 and 10;

e) Optimum temperature;
The optimum temperature is 55° C. at a pH of 9;

f) Temperature resistance:
said acylase retains 905 of its activity after 30 minutes incubation at 50° C.;

g) influences of inhibitors and activators:
inhibitors of serine proteases comprising phenylmethane sulfonylfluoride (0.001 mM), exert an inhibitory action, glycine accelerates the substrate splitting as a function of the concentration;

h) molecular weight:
the molecular weight is approximately 60,000 dalton;

i) subunits:
the molecule consists of only one unit;

j) k$_M$ value:
the K$_M$-value for the substrate N-acetyl-2,3-didehydroleucine is 4.5 mM (30° C., 0.1 M glycine buffer, ph 9).

2. An isolated N-acetyl-2,3-didehydroleucine acylase produced by aerobically cultivating Zoogloea ramigera ABI 1 4306 in an aqueous nutrient medium containing a source for carbon and nitrogen and mineral salts at an initial pH between 7.5 and 9 at 25° to 38° C., then adding an inductor selected from the group consisting of N-acetyl-2,3-didehydroamino acids and further cultivating the mixture aerobically at pH 6.5 and at 28° to 38° C., digesting the cells and purifying the acylase.

3. A method of producing the N-acetyl-2,3-didehydroleucine acylase set forth in claim 1, said method comprising aerobically cultivating Zoogloea ramigera ABI 1 DSM 4306 in an aqueous nutrient medium containing a source for carbon and nitrogen and mineral salts at an initial pH between 7.5 and 9 at 25° to 38° C., then adding an inductor selected from the group consisting of N-acetyl-2,3-didehydroamino acids and further cultivating the mixture aerobically at pH 6.5 and at 28° to 38° C., digesting the cells and purifying the acylase.

* * * * *